(12) United States Patent
Jia et al.

(10) Patent No.: US 7,470,728 B2
(45) Date of Patent: *Dec. 30, 2008

(54) DENTAL GLAZES AND METHOD OF MANUFACTURE AND USE THEREOF

(75) Inventors: Weitao Jia, Wallingford, CT (US); Shuhua Jin, Wallingford, CT (US)

(73) Assignee: Pentron Clinical Technologies LLC, Wallingford, CT (US)

(*) Notice: Subject to any disclaimer, the term of this patent is extended or adjusted under 35 U.S.C. 154(b) by 423 days.

This patent is subject to a terminal disclaimer.

(21) Appl. No.: 11/289,758

(22) Filed: Nov. 29, 2005

(65) Prior Publication Data

US 2006/0111465 A1 May 25, 2006

Related U.S. Application Data

(60) Continuation-in-part of application No. 10/665,391, filed on Sep. 19, 2003, now Pat. No. 7,160,941, which is a continuation-in-part of application No. 10/452,269, filed on Jun. 2, 2003, now Pat. No. 7,241,856, and a continuation-in-part of application No. 10/136,031, filed on Apr. 30, 2002, now Pat. No. 6,653,365, application No. 11/289,758, which is a continuation-in-part of application No. 10/683,750, filed on Oct. 10, 2003, which is a division of application No. 10/287,428, filed on Nov. 4, 2002, now Pat. No. 6,787,629.

(60) Provisional application No. 60/338,116, filed on Nov. 8, 2001, provisional application No. 60/287,918, filed on May 1, 2001.

(51) Int. Cl.
*A61K 6/10* (2006.01)
*C08K 3/10* (2006.01)
*C08K 3/18* (2006.01)

(52) U.S. Cl. ............ 523/109; 524/413; 524/417; 524/430; 524/439; 524/442; 524/443; 524/730

(58) Field of Classification Search ............ 523/109; 524/413, 417, 430, 439, 442, 443, 730
See application file for complete search history.

(56) References Cited

U.S. PATENT DOCUMENTS

| | | |
|---|---|---|
| 3,066,112 A | 11/1962 | Bowen |
| 3,179,623 A | 4/1965 | Bowen |
| 3,194,784 A | 7/1965 | Bowen |
| 3,367,992 A | 2/1968 | Bearden |
| 3,751,399 A | 8/1973 | Lee et al. |
| 3,755,420 A | 8/1973 | Stoffey et al. |
| 3,926,906 A | 12/1975 | Lee, II et al. |
| 4,306,913 A | 12/1981 | Mabie et al. |
| 4,544,359 A | 10/1985 | Waknine |
| 4,547,531 A | 10/1985 | Waknine |
| 4,764,497 A | 8/1988 | Yuasa et al. |
| 5,276,068 A | 1/1994 | Waknine |
| 5,444,104 A | 8/1995 | Waknine |
| 5,484,867 A | 1/1996 | Lichtenhan et al. |
| 5,856,373 A | 1/1999 | Kaisaki et al. |
| 5,865,623 A | 2/1999 | Suh |
| 5,876,210 A | 3/1999 | Klee et al. |
| 5,936,006 A | 8/1999 | Rheinberger et al. |
| 5,969,000 A | 10/1999 | Yang et al. |
| 6,013,694 A | 1/2000 | Jia et al. |
| 6,084,004 A | 7/2000 | Weinmann et al. |
| 6,187,833 B1 | 2/2001 | Oxman et al. |
| 6,187,836 B1 | 2/2001 | Oxman et al. |
| 6,306,926 B1 | 10/2001 | Bretscher et al. |
| 6,362,251 B1 | 3/2002 | Alkemper et al. |
| 6,387,981 B1 | 5/2002 | Zhang et al. |
| 6,417,246 B1 | 7/2002 | Jia et al. |
| 6,572,693 B1 | 6/2003 | Wu et al. |
| 6,653,365 B2 | 11/2003 | Jia |

OTHER PUBLICATIONS

Lichtenhan, Joseph D., "Polyhedral Oligomeric Silsesquioxanes: Building Blocks for Silsesquioxnae-Based Polymers and Hybrid Materials", Comments Inorg. Chem. (1995), vol. 17. No. 2, pp. 115-130.

Lichtenhan, Joseph D., et al, "Linear Hybrid Polymer Building Blocks: Methacrylate-Functionalized Polyhedral Oligomeric Silsesquioxane Monomers and Polymers", Macromolecules (1995) vol. 28, pp. 8435-8437.

NASA High-Performance POSS-Modified Polymeric Composites, NASA Tech Briefs, Feb. 2001, p. 52.

Feher, Frank J., et al, "Silsesquioxanes As Models For Silica Surfaces", American Chemical Society, 1989, vol. 111, pp. 1741-1748.

JP 82-0004646; Publication Date: Jan. 27, 1982 (translation of abstract only).

*Primary Examiner*—Kriellion A Sanders
(74) *Attorney, Agent, or Firm*—Cantor Colburn LLP

(57) ABSTRACT

A polymerizable dental glaze, comprising: a polymerizable, ethylenically unsaturated resin composition; a filler composition consisting essentially of a polyhedral oligomeric silsesquioxane filler; and a curing system. These polymerizable dental glazes may be used for temporary or permanent dental restorations.

19 Claims, No Drawings

DENTAL GLAZES AND METHOD OF MANUFACTURE AND USE THEREOF

CROSS-REFERENCE TO RELATED APPLICATIONS

This application is a continuation-in-part of U.S. patent application Ser. No. 10/665,391 filed Sep. 19, 2003, now U.S. Pat. No. 7,160,941 which is a continuation-in-part of U.S. patent application Ser. No. 10/452,269 filed Jun. 2, 2003 now U.S. Pat. No. 7,241,856 and of U.S. patent application Ser. No. 10/136,031 filed Apr. 30, 2002, now U.S. Pat. No. 6,653,365, which claims the benefit of U.S. Provisional Patent Application Ser. No. 60/287,918 filed May 1, 2001 and U.S. Provisional Patent Application No. 60/338,116, filed Nov. 8, 2001. This application is also a continuation-in-part of U.S. patent application Ser. No. 10/683,750, filed Oct. 10, 2003, which is a divisional of U.S. patent application Ser. No. 10/287,428, filed Nov. 4, 2002, now U.S. Pat. No. 6,787,629. Each of the foregoing is fully incorporated herein by reference.

BACKGROUND

This invention relates to polymerizable dental resins for dental composite materials and the method of manufacture of such resins for restorative dentistry, and more particularly to dental composite materials that are useful as crown and bridge materials either with or without an alloy substrate, as reconstructive materials, restorative materials, filling materials, inlays, onlays, laminate veneers, dental adhesives, cements, sealants and the like. This invention also relates to dental composite materials that are useful as surface sealants and glazes for dental restorations.

In recent years, materials used for dental restorations have principally comprised acrylate or methacrylate resins, hereinafter "(meth)acrylate" resins. Typical (meth)acrylate resin materials are disclosed, for example, in U.S. Pat. No. 3,066,112 to Bowen, U.S. Pat. No. 3,194,784 to Bowen, and U.S. Pat. No. 3,926,906 to Lee et al. An especially important methacrylate monomer is the condensation product of bisphenol A and glycidyl methacrylate, 2,2'-bis[4-(3-methacryloxy-2-hydroxy propoxy)-phenyl]-propane ("Bis-GMA"). Alternatively, Bis-GMA may be synthesized from the diglycidyl ether of bisphenol A and methacrylic acid (see U.S. Pat. No. 3,066,112 to Bowen).

Because the wear and abrasion characteristics and the overall physical, mechanical, and optical properties of these unfilled (meth)acrylate resins is poor, and because (meth)acrylate resin systems exhibit high coefficients of thermal expansion relative to the coefficient of thermal expansion of the tooth structure, these substances by themselves are less than satisfactory. In particular, the disparity in thermal expansion coupled with high shrinkage upon polymerization results in poor marginal adaptability, and ultimately leads to secondary decay. Composite (meth)acrylate dental restorative materials containing (meth)acrylate resins and ceramic fillers were thus developed. These filled compositions are useful for a variety of dental treatments and restorative functions including crown and bridge materials, fillings, adhesives, sealants, luting agents or cements, denture base materials, orthodontic materials and sealants, and other dental restorative materials. Despite their suitability for their intended purposes, however, many of these materials have shrinkages of about two to about 4% by volume upon polymerization.

Alternative resinous materials include the ring-opening polymerization of epoxides. These resins have lower shrinkage than methacrylates, but exhibit compatibility problems with methacrylate bonding adhesives and cements when used together. Epoxy/(meth)acrylate containing compounds containing both epoxy and (meth)acrylate functionality are also known and are obtained from reaction of multi-epoxide containing compound with one or less equivalent of (meth)acrylic acid, or reaction of hydroxyl containing (meth)acrylate with epichlorohydrin. Commercially available epoxy/methacrylate include 3,4-epoxy-cyclohexyl methyl methacrylate from Daicel Chemical, Japan. U.S. Pat. No. 6,187,833 to Oxman et al. generally discloses photocurable compositions containing an epoxy resin, a hydroxyl-containing material, and optionally a free radically polymerizable material. The compositions contain a ternary photoinitiator system comprising an iodonium salt, a visible light sensitizer, and an electron donor compound. Oxman et al. disclose a bifunctional epoxy/acrylate material, but do not disclose an epoxy/acrylate oligomeric material made from the reaction product of a multi-epoxide containing compound and hydroxy (meth)acrylate.

Alternative fillers for restorative dental resin materials have also been developed. Current fillers are glasses, occasionally glass-ceramics and quartz (a crystalline form of silica), particulate polymers and glass-polymer composite particulates. Hybrid filler systems have been developed, based on fillers having an average particle size of 0.6 micrometers or greater in combination with a microfiller having an average particle size of about 0.05 micrometers or less.

Most prior art composite dental restorative materials are intended for permanent dental restorations. The combination of resin and filler are therefore selected to have the desired aesthetic properties, as well as physical properties such a high hardness, low water absorption, low shrinkage, and the like. Composites for temporary dental restorations, on the other hand, have less stringent aesthetic considerations and require slightly different physical properties, including ease of placement and removability. Temporary dental materials thus often have a dull finish that does not blend with natural dentition. The practitioner may also spend less time on surface finishing or polishing because the temporary nature of the restoration.

There accordingly remains a need in the art for dental sealants and glazes that are suitable for use with permanent or temporary composite materials, that are easy to apply, and that will enhance the aesthetic appearance of temporary dental composite restorations.

SUMMARY

A polymerizable dental restorative composition comprises a polymerization product of an oligomer comprising a (meth)acrylate functionality and an epoxy functionality and a filler composition comprising a polyhedral oligomeric silsesquioxane filler and a sol-derived filler.

In one embodiment, the oligomer comprises units of the general structure (I):

wherein A is an organic radical comprising 1 to about 6 (meth)acrylate groups and 0 to about 5 hydroxy groups; and B is an organic radical comprising 1 to about 5 epoxide groups, and A and B are linked through the reaction of an epoxide and a hydroxy group. The polymerizable dental oligomer is conveniently synthesized by the selective reaction of a multifunctional epoxide with a hydroxy (meth)acrylate to yield a reactive, polymerizable dental oligomer having an epoxy functionality and an ethylenically unsaturated functionality.

In another embodiment, the polymerizable dental resin comprises the reaction product of a hydroxy (meth)acrylate of the formula

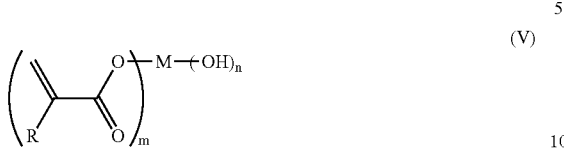

wherein m and n are independently integers of 1 to about 6; M is a substituted or unsubstituted $C_1$ to $C_{33}$ alkyl or aryl group; and R is hydrogen or methyl; and a multifunctional epoxide of the formula

wherein E is a substituted or unsubstituted alkyl, alkoxy, alkylether, heterocycle, alkaryl, or aryl group, and x is an integer of 2 to about 6.

A flowable composition having low shrinkage upon polymerization comprises an oligomer of structure I, specifically structure VIIIa

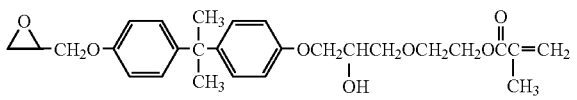

and the above-described filler composition.

In yet another embodiment is a method of manufacturing a polymerizable dental resin comprising reacting, in the presence of a curing system, the above-described hydroxy (meth)acrylate; and multifunctional epoxide.

In another embodiment, a dental restorative material comprises the low shrinkage, polymerizable dental resin comprising an oligomer of structure (I), a filler system, and a curing system. In the formulation of dental restorative materials, both the epoxide functionality and the (meth)acrylate functionality can participate in the polymerization. These two functionalities can be activated simultaneously or one functionality may be activated selectively. The curing system can be a self-cure or a photocure system.

The polymerizable dental resins are used for a variety of dental materials, treatments, and restorative functions, including crown and bridge materials, fillings, adhesives, sealants, luting agents or cements, denture base materials, orthodontic materials and sealants, and other dental restorative materials.

In another embodiment, an improved dental glaze comprises a polymerizable, ethylenically unsaturated resin composition; a filler composition comprising a modified polyhedral oligomeric silsesquioxane filler; and a curing system.

A composition produced by curing a glaze as described herein is also described, as well as a method for forming a temporary dental restoration using a glaze.

DETAILED DESCRIPTION OF PREFERRED EMBODIMENTS

It has unexpectedly been discovered that a polymerizable dental resin oligomer having both an epoxy functionality and a (meth)acrylate functionality has improved low shrinkage upon curing, together with improved fracture resistance. Furthermore, it has been discovered that the use of a cationic initiator in the polymerization of the dental resin is not necessary, although it may optionally be used.

In one embodiment the resin may be used in combination with a filler composition, including one or more of a nanosized polyhedral oligomeric silsesquioxane (POSS) filler, a nanosized filler derived from a sol-gel process, or a conventional dental composite filler material.

In another embodiment, a dental glaze is described, comprising a polymerizable, ethylenically unsaturated resin composition and a filler composition comprising a modified polyhedral oligomeric silsesquioxane filler.

As used herein, the term "(meth)acrylate" is intended to encompass both acrylate and methacrylate groups. The term "multifunctional epoxide" is intended to encompass an organic compound comprising at least two epoxide functionalities. The term "hydroxy (meth)acrylate" is intended to encompass an organic compound comprising at least one hydroxy functionality and at least one (meth)acrylate functionality.

In particular, an unexpectedly improved polymerizable oligomer comprises units of structure (I)

wherein A is an organic radical comprising 1 to about 6 (meth)acrylate groups and 0 to about 5 hydroxy groups; and B is an organic radical comprising 1 to about 5 epoxide groups, wherein A and B are linked through the reaction of an epoxide and a hydroxy group. The general structure of (I) can have a variety of forms, for example A and B can be in alternating order (e.g., ABAB . . . ) and/or branched. In one embodiment, the oligomer has the form $A_aB_b$ wherein a is an integer from 2 to 10, b is one, A is a monovalent radical, and B is a radical having a valency corresponding to a. In another embodiment, a is 1, b is an integer from 2 to 10, A is a radical having a valency corresponding to b, and B is a monovalent radical.

The oligomer (I) is synthesized from the reaction of a multifunctional epoxide and a hydroxy (meth)acrylate in the presence of a catalyst and heat. Preferably the amount of hydroxy groups in the hydroxy (meth)acrylate is less than one equivalent per equivalent of epoxide. Depending upon the reaction conditions, such as ratio of hydroxy to epoxy, the reaction temperature and time, and the amount of catalyst, the reaction product may comprise a variety of one or more compounds, including the unreacted epoxides and hydroxy (meth)acrylates, the oligomer of structure (I), and a polymeric epoxy/(meth)acrylate or polyepoxides resulting from the ring-opening of the epoxides.

Suitable multifunctional epoxides are compounds having two or more epoxide (oxirane) functionalities, and include monomeric epoxy compounds and epoxides of the oligomeric or polymeric type, which can be aliphatic, cycloaliphatic, aromatic, or heterocyclic. These multifunctional epoxides may vary from low molecular weight monomeric materials to oligomers to high molecular weight polymers and may vary greatly in the nature of their backbone and substituent groups, provided that the backbone and the substituents thereon can be molecular groups that do not substantially interfere with the cure of the polymerizable dental resin at room temperature. Illustrative of permissible substituent groups include halogens, ester groups, ethers, sulfonate groups, siloxane groups, nitro groups, phosphate groups, and the like.

The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl (meth)acrylate polymer or copolymer). These epoxides generally have, on average, greater than or equal to about two polymerizable epoxy groups per molecule. The "average" number of epoxy groups per molecule is determined by dividing the total number of epoxy groups in the multifunctional epoxide by the total number of epoxy-containing molecules present.

The epoxides may be pure compounds or may be mixtures of compounds having greater than or equal to about two polymerizable epoxy groups per molecule. The number average molecular weight ($M_n$) of the epoxy-containing materials is about 58 to about 20,000 g/mole. Examples of mixtures include two or more multifunctional epoxides having different number average molecular weight distributions of epoxy-containing compounds, such as a low molecular weight (below 200 g/mole) blended with an intermediate molecular weight (about 200 to about 1,000 g/mole) and/or higher molecular weight (above about 20,000 g/mole). Alternatively or additionally, the multifunctional epoxide may comprise a blend of multifunctional epoxides having different chemical natures, such as aliphatic and aromatic, or functionalities, such as polar and non-polar.

Useful multifunctional epoxides include those that contain cyclohexene oxide groups such as epoxycyclohexanecarboxylates, typified by 3,4-epoxycyclohexylmethyl-3,4-epoxycyclohexanecarboxylate; 3,4-epoxy-2-methylcyclohexylmethyl-3,4-epoxy-2-methylcyclohexane carboxylate; and bis(3,4-epoxy-6-methylcyclohexylmethyl) adipate.

Other multifunctional epoxides that are of particular utility in forming the polymerizable dental resins include the formula (II)

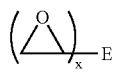

(II)

wherein E is a substituted or unsubstituted alkyl, alkoxy, alkylether, heterocycle, alkaryl, or aryl group and x is an integer of 2 to about 6. Suitable substitutions on the E moiety include, but are not limited to, linear or branched, saturated or unsaturated $C_1$-$C_{12}$ alkyl; cyclic $C_3$-$C_7$ alkyl; halogens; ester groups; ether groups; amide groups; aryl; and the like.

In particular, the multifunctional epoxide may have the formula (III):

(III)

wherein Y is a divalent $C_1$-$C_{33}$ substituted or unsubstituted alkyl, alkoxy, aryl, alkylether, heterocycle, or alkaryl group, and q is 0 to about 20. Preferably, Y is a divalent $C_6$-$C_{18}$ aryl or $C_1$-$C_{33}$ alkyl or alkylether-containing group, and q is an integer of 0 to about 10. Suitable substitution on the Y moiety include, but is not limited to, linear or branched, saturated or unsaturated $C_1$-$C_{12}$ alkyl; cyclic $C_3$-$C_7$ alkyl; halogens; ester groups; ether groups; amide groups; aryl; and the like.

A particularly preferred multifunctional epoxide is an aromatic diglycidyl ether having the formula (IV):

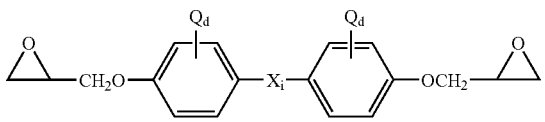

(IV)

wherein X is oxygen, sulfur, carbonyl, or a divalent $C_1$-$C_6$ alkyl, alkylether, or aryl group, d is an integer of 1 to 4, and i is an integer of 0 to about 6. Preferably, X is a divalent alkyl or alkylether-containing group. Q is hydrogen or halogen, such as chlorine, bromine, and iodine; and d is an integer of 2, 3, or 4. Preferably Q is hydrogen or bromine.

Further examples of suitable multifunctional glycidyl ethers are the glycidyl ethers of polyhydric phenols obtained by reacting a polyhydric phenol with an excess of a chlorohydrin such as epichlorohydrin, e.g., the diglycidyl ether of 2,2-bis-(2,3-epoxypropoxyphenol)-propane (Bisphenol A); brominated diglycidyl ether of bisphenol A, the diglycidyl ether of Bisphenol F; the 1,4-butanediol diglycidyl ether of phenolformaldehyde novolak (e.g., "DEN-431" and "DEN-438" from Dow Chemical Company); resorcinol diglycidyl ether (e.g., "KOPOXITE" from Koppers Company, Inc.); and polyfunctional glycidyl ethers such as the diglycidyl ether of 1,4-butanediol, the diglycidyl ether of neopentyl glycol, the diglycidyl ether of cyclohexanedimethanol, trimethylol ethane triglycidyl ether, trimethylol propane triglycidyl ether, and mixtures comprising at least one of the foregoing ethers.

The hydroxy (meth)acrylate compounds used to synthesize the oligomer of the may contain a hydroxyl group terminally situated or pendent from a polymeric or copolymeric (meth)acrylate. A general structure of the hydroxy (meth)acrylate is shown in formula (V):

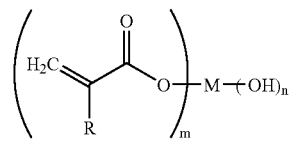

(V)

wherein m and n are independently integers from 1 to 6; M is a substituted or unsubstituted $C_1$-$C_{33}$ alkyl or aryl group; and R is hydrogen or methyl. Suitable substitution on the M moiety include, but is not limited to, linear or branched, saturated or unsaturated $C_1$-$C_{12}$ alkyl; cyclic $C_3$-$C_7$ alkyl; halogens; ester groups; ether groups; amide groups; aryl; and the like.

A preferred hydroxy (meth)acrylate is a linear monofunctional hydroxy (meth)acrylate wherein m and n equal 1, as shown in formula (VI):

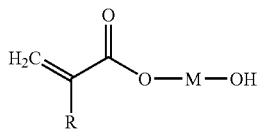
(VI)

Non-limiting examples of suitable hydroxy (meth)acrylates include caprolactone 2-(methacryloyloxy) ethyl ester (CLMA); 2-hydroxyethyl acrylate; 2-hydroxyethyl methacrylate (HEMA); 3-hydroxypropyl (meth)acrylate; 4-hydroxybutyl (meth)acrylate; polyethylene glycol mono(meth)acrylate; glycerol di(meth)acrylate; trimethylolpropane di(meth)acrylate; pentaerythritol tri(meth)acrylate; and the (meth)acrylate of phenyl glycidyl ether. Blends of the aforementioned hydroxy (meth)acrylates can also be used to form the polymerizable dental resin. The most preferred hydroxy acrylate or hydroxy methacrylate is CLMA and HEMA.

In one preferred embodiment, reaction of multifunctional epoxy (IV) with monofunctional hydroxy (meth)acrylate (VI) yields a reaction product comprising a mixture of products, including a polymerizable oligomer having the structure (VII):

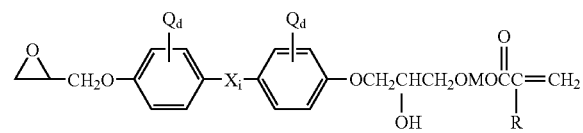
(VII)

wherein X, M, R, Q, d, and i are as defined above.

Further non-limiting examples of preferred polymerizable oligomers include the structures (VIII), and (IX):

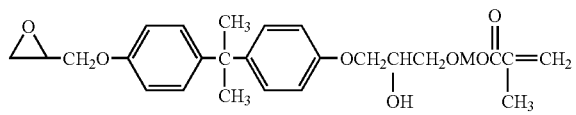
(VIII)

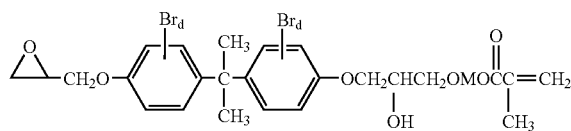
(IX)

wherein M is a divalent linear $C_2$-$C_4$ alkyl group, a divalent linear $C_1$-$C_{10}$ alkoxy group, e.g., $(-OCH_2CH_2-)_{1-10}$, or a $C_2$-$C_{10}$ divalent linear ester group, e.g., $-(CH_2)_4C(O)OCH_2CH_2$. In a specific embodiment, M is ethylene, $(-CH_2-CH_2-)$, this oligomer being referred to herein as "BAHEMA".

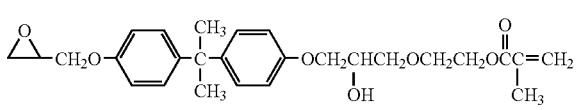
(VIIIa)

In still another embodiment, the oligomer has the structure (X):

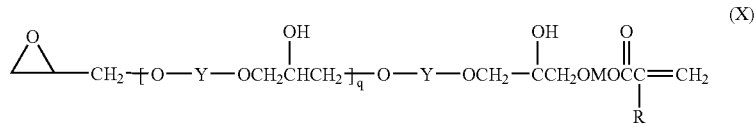
(X)

wherein Y is a divalent $C_1$ to $C_{33}$ substituted or unsubstituted alkyl, alkoxy, aryl, alkylether, heterocyclic, or alkaryl group; M is a substituted or unsubstituted $C_1$-$C_{33}$ alkyl or aryl group; R is hydrogen or methyl; and q is 0 to about 20.

In yet another embodiment, the oligomer has the structure (XI)):

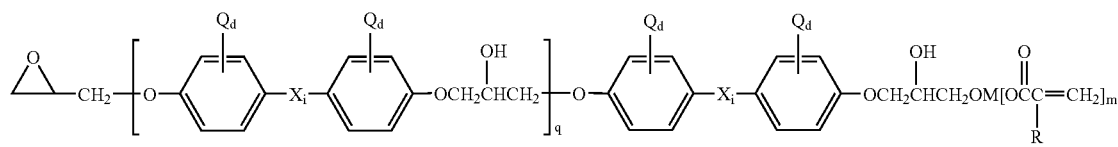
(XI)

wherein m is 1 to 3, preferably 1; X is oxygen, sulfur, carbonyl, or a divalent substituted or unsubstituted $C_1$-$C_6$ alkyl or aryl group; i is 0 to about 6; Q is hydrogen, chlorine, bromine or iodine; q is 0 to about 20; M is a substituted or unsubstituted $C_1$-$C_{33}$ alkyl or aryl group; R is hydrogen or methyl; and d is 2, 3, or 4.

In the formation of the oligomers, the amount of hydroxy (meth)acrylate is selected so as to result in the polymerizable resin having a molar ratio of epoxy:(meth)acrylate groups of about 1:10 to about 10:1, preferably about 1:5 to about 5:1, more preferably about 2:1 to about 1:2. Suitable amounts may be readily selected by one of ordinary skill in the art, depending on the reactivity of the epoxide and hydroxy (meth)acrylate compounds, reaction conditions, and the like. Suitable reaction conditions are known to those of skill in the art.

The catalyst can be selected from those used in conventional cationic, anionic or coordination ring-opening polymerization. Preferred catalysts are metal organic catalysts comprising tin or titanium. Suitable non-limiting examples of tin-containing catalysts are dibutyltin dilaurate, dibutyltin maleate, dibutyltin diacetate, dioctyltin maleate, dibutyltin phthalate, stannous octoate, stannous naphthenate, stannous stearate, stannous 2-ethyl hexanoate, dibutyltin diacetylacetonate, dibutyltin oxide, and combinations comprising at least one of the foregoing tin based catalysts. Suitable non-limiting examples of titanium-based catalysts are tetrabutyl titanate, tetrapropyl titanate, tetraisopropyl titanate, triethanolamine titanate, titanium tetraacetylacetonate, and combinations comprising at least one of the foregoing titanium based catalysts. The preferred catalysts are stannous octoate or stannous 2-ethyl hexanoate.

It is generally desirable to use the catalyst in an amount of about 0.10 to about 10 mole percent (mole %) based on the total moles of the reactant mixture. Within this range it is generally desirable to utilize the catalyst in an amount of greater than or equal to about one, preferably greater than or equal to about 2, and most preferably greater than or equal to about 3 mole % based on the total moles of the reactants. Within this range, it is generally desirable to utilize the catalyst in an amount of less than or equal to about 8, and preferably less than or equal to about 7 mole % based on the total moles of the reactants.

The above-described polymerizable dental resin can be used together with a curing system, other optional viscous resins, optional diluents, and/or an optional filler system to provide a dental restorative material for the formation of dental restorations. It is generally desirable to use the above-described polymerizable dental resin in an amount of about 1 to about 99 weight percent (wt %) based on the total weight of the dental restorative material. Within this range it is generally desirable to use the polymerizable dental resin in an amount of greater than or equal to about 10, preferably greater than or equal to about 30, and most preferably greater than or equal to about 50 wt % based on the total weight of the dental restorative material. Within this range, it is generally desirable to utilize the polymerizable dental resin in an amount of less than or equal to about 95, and preferably less than or equal to about 90 wt % based on the total weight of the dental restorative material.

Known viscous resins may be added to the polymerizable dental resin to provide a dental restorative material. Non-limiting examples include polyurethane dimethacrylates (PUDMA), diurethane dimethacrylates (DUDMA), and/or the polycarbonate dimethacrylate (PCDMA) disclosed in U.S. Pat. Nos. 5,276,068 and 5,444,104 to Waknine, which is the condensation product of two parts of a hydroxyalkyl-methacrylate and 1 part of a bis(chloroformate). Another advantageous resin having lower water sorption characteristics is an ethoxylated bisphenol a dimethacrylate (EBPDMA) as disclosed in U.S. Pat. No. 6,013,694. An especially useful methacrylate resin is the condensation product of bisphenol A and glycidyl methacrylate, 2,2'-bis[4-(3-methacryloxy-2-hydroxy propoxy)-phenyl]-propane (Bis-GMA).

Diluent monomers may be used to increase the surface wettability of the composition and/or to decrease the viscosity of the polymerization medium. Suitable diluent monomers include those known in the art such as hydroxy alkyl methacrylates, for example 2-hydroxyethyl methacrylate and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; and diol dimethacrylates such as butanedimethacrylate, dodecanedimethacrylate, or 1,6-hexanedioldimethacrylate (HDDMA). Tri(ethylene glycol) dimethacrylate (TEGDMA) is particularly preferred.

Diluent monomers or viscous resins, when present, are incorporated into the dental restorative materials in an amount of about 1 to about 70 wt % of the total dental restorative material.

In one embodiment the filler composition comprises a specific combination of inorganic fillers, in particular a combination of a nanosized polyhedral oligomeric silsesquioxane (POSS) filler and a nanosized filler derived from a sol-gel process, optionally together with a conventional dental composite filler material.

When used as a dental glaze, the filler comprises a nanosized polyhedral oligomeric silsesquioxane (POSS) filler.

Polyhedral oligomeric silsesquioxane fillers are of the generic formula $(RSiO_{3/2})_n$, wherein R is a hydrocarbon and n is 6, 8, 10, 12, or higher. Such POSS materials are commercially available, for example from Hybrid Plastics. These molecules have rigid, thermally stable silicon-oxygen frameworks with an oxygen to silicon ratio of 1.5, and covalently-bound hydrocarbon groups that provide an organic outer layer. In one embodiment, R is a $C_1$-$C_{24}$ straight, branched, or cyclic alkyl group, or a $C_6$-$C_{24}$ aromatic, alkylaryl, or arylalkyl group, wherein the alkyl or aromatic groups are optionally substituted with $C_1$-$C_6$ alkyl, halo, $C_1$-$C_6$ alkoxy, $C_1$-$C_6$ perhaloalkyl, and the like. Specific exemplary groups include, phenyl, isooctyl, cyclohexyl, cyclopentyl, isobutyl, or other groups. Such silsesquioxanes include, for example, dodecaphenyl-POSS, octaisooctyl-POSS, octacyclohexyl-POSS, octacyclopentyl-POSS, octaisobutyl-POSS and the like. POSS typically have surface areas greater than 400 square meters per gram ($m^2$/gm).

Polyhedral oligomeric silsesquioxanes as used herein further includes monomers of the general formula $R_{n+p}T_{n-p-1}D_p(OL)_p$, wherein R is as defined above, T is $SiO_{3/2}$, D is $SiO_{2/2}$, L is hydrogen or a hydrocarbon comprising a functional group, and p is a multiple of 3. An exemplary compound of this type has the formula $R_7T_4D_3(OL)_3$.

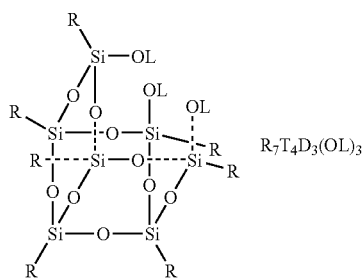

In a specific embodiment, each R is a phenyl group and each L is a hydrogen, providing a compound of the formula $(Ph)_7(SiO_{1.5})_4D_3(OH)_3$. One such filler material is commercially available from Hybrid Plastics, Inc. under the designation POSS SO 1458. In another specific embodiment, L is an organic group containing a functional group that may or may be reactive with a component of the resin composition, for example a functional group such as a halide, alcohol, amine, isocyanate, acid, acid chloride, silanol, silane, (meth)acrylate, olefin, epoxide, and the like. The organic group is a divalent group of 1 to 36 carbon atoms that serves as a linker between the D groups and the functional group.

Other types of functionalized POSS fillers may also be used, and include those of the general formula $R_{n-m}T_nF_m$ wherein R is a hydrocarbon; n is 6, 8, 10, 12 or higher; m is 1 to n; T is $SiO_{1.5}$, and F is an organic group comprising a functional group, wherein the functional group includes, for example, halide, alcohol, amine, isocyanate, acid, acid chloride, silanols, silane, acrylate, methacrylate, olefin, epoxide, and the like. One, two, or more of the functional groups may be reactive with at least one component of the resin composition. In some cases, it is possible to have all of the covalently bound organic groups be reactive groups.

Such compounds, may be prepared, for example, by corner-capping an incompletely condensed POSS containing trisilanol groups with a substituted trichlorosilane. For example, the trisilanol functionality of $R_7T_4D_3(OH)_3$, can be reacted with $Cl_3Si$—F to produce the fully condensed POSS monomer $R_7T_8F$:

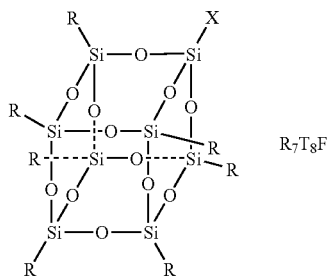

$R_7T_8F$

Through variation of the F group on the silane, a variety of functional groups can be placed at the corner of the POSS framework, including but not limited to halide, alcohol, amine, isocyanate, acid, acid chloride, silanols, silane, acrylate, methacrylate, olefin, and epoxide.

Preferred functional groups F are acrylate (—X—OC(O)CH=$CH_2$) and methacrylate (—X—OC(O)CH($CH_3$)=$CH_2$) groups, wherein X is a divalent linking group having 1 to about 36 carbons, such as methylene, ethylene, propylene, isopropylene, butylene, isobutylene, phenylene, and the like. X may also be substituted with functional groups such as ether (e.g., —$CH_2CH_2OCH_2CH_2$—), as long as such functional groups do not interfere with formation or use of the POSS. X is preferably propylene, isobutylene, or —OSi$(CH_3)_2CH_2CH_2CH_2$—. One, all, or an intermediate number of the covalently bound groups may be acrylate or methacrylate groups. Such functionalized POSS are available from Gelest, Inc. (Tullytown, Pa.) and Hybrid Plastics. A methacryloxypropyl-substituted $T_8$ POSS (wherein all positions of the polyhedron are methacryloxypropyl-substituted) is available under the trade designation MA0735 from Hybrid Plastics Corp.). Another methacryloxypropyl-substituted $T_8$ POSS (wherein one position is methacryloxypropyl-substituted and the remaining positions are isobutyl-substituted) is available under the trade designation MA0702 from Hybrid Plastics Corp (Fountain Valley, Calif.).

The linking groups X are also suitable for use with other functional groups. Other POSS fillers include, for example $T_6$, $T_8$, $T_{10}$, or $T_{12}$ structures functionalized with alkoxysilanes such as diethoxymethylsilylethyl, diethoxymethylsilylpropyl, ethoxydimethylsilylethyl, ethoxydimethylsilylpropyl, triethoxysilylethyl, and the like; with styrene, such as styrenyl ($C_6H_5CH=CH$—), styryl (—$C_6H_4CH=CH_2$) and the like; with olefins such as allyl, —OSi$(CH_3)_2$$CH_2CH_2$=$CH_2$, cyclohexenylethyl, —OSi$(CH_3)_2CH=CH_2$ and the like; with epoxies, such as 4-propyl-1,2-epoxycyclohexyl, (2-(7-oxa-bicyclo[4.1.0]heptan-3-yl)ethylene, 3-propoxy, glycidyl, (—$CH_2CH_2CH_2OCH_2CH(O)CH_2$), —OSi$(CH_3)_2CH_2CH_2CH_2OCH_2CH(O)CH_2$, and the like; with chlorosilanes such as chlorosilylethyl, dichlorosilylethyl, trichlorosilylethyl, and the like; with amines such as aminopropyl, aminoethylaminopropyl, and the like; with alcohols and phenols such as —OSi$(CH_3)_2CH_2CH_2CH_2OC(CH_2CH_3)_2(CH_2CH_2OH)$, 4-propylene-trans-1,2-cyclohexanediol, —$CH_2CH_2CH_2OCH_2C(CH_2OH)_2(OH)$, —OSi$(CH_3)_2CH_2CH_2CH_2OC(CH_2OH)_2(CH_2CH_3)$, and the like; with phosphines such as diphenylphosphinoethyl, diphenylphosphinopropyl, and the like; with norbornenyls such as norbornenylethyl; with nitriles such as cyanoethyl, cyanopropyl, —OSi$(CH_3)_2CH_2CH_2CH_2CN$, and the like; with isocyanates such as isocyanatopropyl, —OSi$(CH_3)_2$$CH_2CH_2CH_2NCO$, and the like, with halides such as 3-chloropropyl, chlorobenzyl (—$C_6H_4CH_2Cl$), chlorobenzylethyl, 4-chlorophenyl, trifluoropropyl (including a $T_8$ cube with eight trifluoropropyl substitutions) and the like; and with esters, such as ethyl undecanoat-1-yl and methyl propionat-1-yl, and the like. Certain polymers such as poly(dimethyl-comethylhydrido-co-methylpropyl polymers, poly(dimethyl-comethylvinyl-co-methylethylsiloxy, poly(ethylnorbonenyl-co-norbonene) and poly(ethylsilsesquioxan) may also be used to functionalize POSS. Many of these substitutions are commercially available on $T_8$ POSS from Hybrid Plastics.

Without being bound by theory, it is hypothesized that the functionalization of the cubes allow for better dispersion in and reactivity with the matrix resin, which reduces moisture uptake, as well as volumetric shrinkage. Bonding of the $T_8$ cubes with the matrix resin may be achieved by co-polymerization with the resin monomers or oligomers in the presence of a cure system, for example by treatment with radiation such as UV light.

Alternatively, the POSS monomer comprising at least one F group may further be synthetically modified to form a "modified POSS." For example, a POSS monomer according to the general formula $R_7T_8F$ may be converted to a modified POSS of formula $R_7T_8J$ by the reaction of the reactive functionality of the F group with an organic compound (J*) which comprises two or more reactive functionalities to result in a J group, which is the reaction product of S and J*. J preferably comprises one or more functional groups that are reactive with at least one component of the resin composition. Reactive groups suitable for the functional group of J include, for example, halide, alcohol, amine, isocyanate, acid, acid chloride, silanols, silane, acrylate, methacrylate, olefin, and epoxide. The particular methods by which the functional group F can be synthetically modified to result in J groups can readily be determined by one of ordinary skill in the art without undue experimentation. An example of preparing a modified POSS includes reacting a POSS monomer according to the formula $R_7T_8F$ wherein the functional group on S is an epoxide with one equivalent of J* which is a (meth)acrylic acid in the presence of an appropriate catalyst and solvent, and optional heating. The resulting modified POSS would be the reaction product $R_7T_8J$ wherein the J group comprises (meth)acrylate functionality and the secondary hydroxy from the ring opening reaction.

Alternatively, depending upon the POSS monomer starting material, the J* compound, the ratios of the two starting materials, and reaction conditions, the modified POSS may be in the form of a monomer, oligomer, polymer, or a mixture of reaction products including at least one of the foregoing compounds. For instance, a POSS monomer according to the general formula $R_{n-m}T_nF_m$ wherein m is 2 or more, may further be synthetically modified to form a modified POSS of formula $R_{n-m}T_nS_{m-p}J_p$ by the reaction with one or more equivalents of organic compound (J*). The p may be an integer from 1 to m, wherein m and n have been defined above. Adjusting the molar ratios of Y to J* may result in a mixture of reaction products comprising partial or complete conversion of the Y groups to J in addition to further polymerized products.

In yet another example, starting with a POSS of the general formula $R_7T_4D_3(OL)_3$, adjusting the molar ratios of the L functional groups to the reactive organic group (J*) results in partial to complete conversion of L groups to J groups. For example, one equivalent of $R_7T_4D_3(OL)_3$, wherein the functional group of L is an epoxide, is reacted with one equivalent of J* which is (meth)acrylic acid, or a methacrylate terminated carboxylic acid, wherein the ratio of epoxide to (meth)acrylic acid or (meth)acrylate terminated carboxylic acid is 3 to 1, to form a ring opened product. The resulting modified POSS would include the reaction product $R_7T_4D_3(OL)_2(OJ)$ wherein the L group comprises epoxy functionality and the J group comprises (meth)acrylate functionality. Again, the resulting modified POSS may also include other reaction products, such as the product resulting from the reaction of the secondary hydroxyl of the ring-opened epoxide with another epoxy ring of a L group to form a polymerized product. By controlling the reaction conditions, such as ratio of J* to Y groups, the reaction temperature and time, and the amount of catalyst, the reaction product may comprise a variety of one or more compounds, including modified POSS monomer, oligomer, and/or polymers.

The ratio of F or L functional groups to J* functional groups in a reaction mixture may be selected to control the outcome of the desired product. Exemplary ratios of F or L functional groups to J* may be about 10:1 to about 1:10, preferably about 5:1 to about 1:5; more preferably about 2:1 to about 1:2, and even more preferably about 1:1.

In one embodiment, the POSS monomer used to prepare the modified POSS comprises an F or g group having a functional group which includes epoxy, hydroxy, phenol, and the like. Within this embodiment, the J* compounds comprise at least one (meth)acrylate functionality and further functional groups that may react with the functional groups of S or Y, including epoxy, carboxylic acid, hydroxy, phenol, and the like.

When the functional group of F or L is epoxy, the preferred organic compound J* used to prepare the modified POSS is a (meth)acrylate terminated carboxylic acid or a hydroxy (meth)acrylate. Hydroxy(meth)acrylate as used herein includes compounds of the general formula

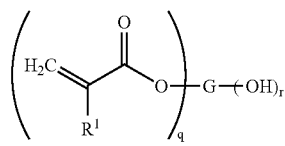

wherein q and r are independently integers from 1 to 6; G is a substituted or unsubstituted $C_1$-$C_{33}$ alkyl, substituted or unsubstituted aryl group, or ($C_1$-$C_6$) alkyl-oxy-($C_1$-$C_6$) alkyl; and $R_1$ is hydrogen or methyl. Suitable substitution on the G moiety includes, for example, linear or branched, saturated or unsaturated $C_1$-$C_{12}$ alkyl; $C_1$-$C_{12}$ alkoxy; cyclic $C_3$-$C_7$ alkyl; halogens; ester groups; ether groups; amide groups; aryl; and the like. A preferred hydroxy (meth)acrylate is where q is 1 and r is 1.

Non-limiting examples of suitable hydroxy (meth)acrylates include caprolactone 2-(methacryloyloxy) ethyl ester (CLMA); 2-hydroxyethyl acrylate; 2-hydroxyethyl methacrylate (HEMA); 3-hydroxypropyl (meth)acrylate; 4-hydroxybutyl (meth)acrylate; polyethylene glycol mono(meth)acrylate; glycerol di(meth)acrylate; trimethylolpropane di(meth)acrylate; pentaerythritol tri(meth)acrylate; and the (meth)acrylate of phenyl glycidyl ether. Blends of the aforementioned hydroxy (meth)acrylates can also be used to form the polymerizable dental resin. The most preferred hydroxy acrylate or hydroxy methacrylate is CLMA and HEMA.

In another embodiment, J* is a molecule comprising at least one epoxy group and at least one (meth)acrylate group. Exemplary J* groups of this type include glycidyl (meth)acrylate; 2-((oxiran-2-yl)methoxy)ethyl acrylate; 3-((oxiran-2-yl)methoxy)propyl acrylate; and the like. Within this embodiment, the S or Y functional group of the POSS monomer is preferably hydroxy, phenol, or carboxyl.

The catalyst used in the epoxide ring opening reaction to form the modified POSS may be selected from those used in conventional cationic, anionic or coordination ring-opening polymerization. Preferred catalysts are metal organic catalysts comprising tin or titanium. Suitable non-limiting examples of tin-containing catalysts are dibutyltin dilaurate, dibutyltin maleate, dibutyltin diacetate, dioctyltin maleate, dibutyltin phthalate, stannous octoate, stannous naphthenate, stannous stearate, stannous 2-ethyl hexanoate, dibutyltin diacetylacetonate, dibutyltin oxide, and combinations comprising at least one of the foregoing tin based catalysts. Suitable non-limiting examples of titanium-based catalysts are tetrabutyl titanate, tetrapropyl titanate, tetraisopropyl titanate, triethanolamine titanate, titanium tetraacetylacetonate, and combinations comprising at least one of the foregoing titanium based catalysts. The preferred catalysts are stannous octoate or stannous 2-ethyl hexanoate.

It is generally desirable to use the catalyst in an amount of about 0.10 to about 10 mole percent (mole %) based on the total moles of the reactant mixture. Within this range it is generally desirable to utilize the catalyst in an amount of greater than or equal to about one, preferably greater than or equal to about 2, and most preferably greater than or equal to about 3 mole % based on the total moles of the reactants. Within this range, it is generally desirable to utilize the catalyst in an amount of less than or equal to about 8, and preferably less than or equal to about 7 mole % based on the total moles of the reactants.

In a preferred embodiment, the modified POSS comprises (meth)acrylate functionality or a combination of epoxy and (meth)acrylate functionality.

Combinations comprising one or more of the foregoing POSS fillers may be used.

In addition to the POSS filler, a second nanoscale filler derived from a silica sol can be used. These fillers are produced by drying, heating, and preferably silanizing an aqueous or organic sol of silica particles to form a filler material referred to hereinafter as the "sol derived filler." The aqueous sol contains about 15 to about 30 percent of amorphous, elongated, bound silica particles in an aqueous solution. The silica particles have average diameters of about 5 to about 50 nanometers, specifically about 10 to about 30 nanometers, more specifically about 5 to about 20 nanometers. The particles may be bound to each other so as to result in chains having lengths of about 10 about 400 nanometers, specifically about 20 to about 300 nanometers preferred, more specifically about 40 to about 200 nanometers. Such silica is commercially available as a colloidal silica sol in water form Nissan Chemical Industries, Ltd, under the trade names SNOWTEX-PS-S™, SNOWTEX-PS-M™, SNOWTEX-PS-L™, and MA-ST-UP™, all from Nissan Chemical Company. Without being bound by theory, it is hypothesized that the "strings" or "pearls" of bound silica improve fracture resistance compared to discrete, particulate materials. U.S. Pat. No. 6,417,246 discloses suitable filler compositions and is hereby incorporated by reference.

The (aqueous or organic) sol of silica is initially dried at a temperature to remove the liquid (e.g., water, methanol, or the like) present. The temperature range for drying may be from about 30 to about 200° C. Thereafter, the dried powder is heated at about or above about 600° C. Preferably, the powder is heated at about or above about 800° C. to produce a silica filler having a least one crystalline phase, and preferably a mixture of crystalline and amorphous phases. Heat treatment of the powder produced from the aqueous or organic sol produces a filler having increased strength, due to the formation of the crystalline phase(s). An x-ray diffractometer is used to determine the formation or presence of crystal phases present. Without being bound by theory, the particles retain nanostructured character.

In order to improve bonding of the filler with a resin matrix, the heat-treated silica particles are preferably treated with a silane, for example gamma-mercaptopropyltrimethoxysilane, gamma-mercaptopropyltriethoxysilane, gamma-aminopropyltriethoxysilane, and the like. The material is then ready for mixture with other filler or the resin material for manufacture of a dental composite.

In yet another embodiment, an aqueous or organic silica sol, as described above, is mixed with one or more other particulate filler materials during the treatment process to form what is referred to hereinafter as "a sol-derived hybrid filler", preferably comprising some particles that are nano-sized and microsized. Preferably a mixture of the (untreated) nanoparticulate silica sol is combined with a micro-particulate filler. Other conventional additives may also be included in the mixture, such as, but not limited to radiopaquing or opacifying agents. The micro-particulate filler contains particles having sizes of about 0.1 to about 5 micrometers, specifically about 0.2 to about 4 micrometers, and more specifically about 0.6 to about 1 micrometer (all particles in the micrometer ranges being referred to as micro-particulates). Examples of suitable micro-particulate glass or ceramic filling materials include, but are not limited to, silica, silicate glass, quartz, barium oxide, barium silicate, strontium silicate, barium borosilicate, strontium borosilicate, borosilicate, lithium silicate, lithium alumina silicate, zinc oxide, calcium oxide, tantalum dioxide, amorphous silica, ammoniated or deammoniated calcium phosphate and alumina, zirconia, tin oxide and titania. Examples of commercially available ground dental glass fillers having particles sizes in the range of about 0.5 to about 2 micrometers are sold under the trade names 8235™, GM27884™, and in other particles sizes are sold under the trade names FK 0.4™, FK 0.7™, FK 1.0™, FK 1.5™ etc., all from Schott Glas. The mixture may further comprise unbound silicate colloids of about 0.001 to about 0.07 micrometers.

The process of producing a sol-derived hybrid filler of nano- and micro-particulate fillers includes preparing an aqueous or organic solution of a micro-particulate glass or ceramic filler under acidic or neutral conditions (up to about a pH of 7) and preferably under acidic conditions or with a pH of from about 1 to about 4. The micro-particulate filler is dispersed into the solution by means of stirring, sonification or other proper means or their combinations. Next, an aqueous or organic silica sol is gradually added into the above solution while stirring to form a gel. The gel is then dried, preferably in shallow pans or in thin films, with a conventional gravity-drying oven for a slow drying or furnace for quick drying at a temperature to remove the liquid present. The temperature range for drying may be from about 30 to about 200° C. The dried powders are then collected and pulverized. The powder is next fired at a temperature and time sufficient to fuse the nano-particulate pearl-like silica onto the micro-particulate glass or ceramic surfaces. The dried powder may be heated at about or above about 600° C. and preferably, the powder is heated at about or above about 800° C. to fuse the nano-particulate pearl-like silica onto the micro-particulate glass or ceramic surfaces. The fired particles are further subject to pulverization or milling to break the agglomerates and surface silane treatment to improve bonding of the filler with a resin matrix. Examples of silanes useful herein include, but are not limited to, gamma-mercaptopropyltrimethoxysilane, gamma-mercaptopropyltriethoxysilane, gamma-aminopropyltriethoxysilane, and the like. In these sol-derived hybrid fillers, the portion of material derived from the sol is present in an amount of less than or equal to about 90 percent by weight based on the total weight of the filler, with less than or equal to about 80 percent by weight preferred, and less than or equal to about 70 percent by weight more preferred. Also preferred is the portion of material derived from the sol present in an amount of greater than or equal to about 40 percent by weight, with greater than or equal to about 50 percent by weight more preferred, and greater than or equal to about 60 percent by weight based on the total weight of the filler especially preferred. The micro-particulate filler is present in an amount of less than or equal to about 20 percent by weight, with less than or equal to about 10 percent by weight preferred, and less than or equal to about 5 percent by weight more preferred. Also preferred is the micro-particulate filler present in an amount of greater than or equal to 0 percent by weight, with greater than or equal to about 1 percent by weight more preferred, and greater than or equal to about 2 percent by weight especially preferred.

In yet another embodiment herein, another type of sol-derived hybrid filler is derived from an aqueous or organic solution of an opacifying metal oxide or calcinable precursor compound including, but not limited to, zirconia, zirconium acetate, bismuth acetate, bismuth oxychloride, or the like. This hybrid filler is prepared under acidic or neutral conditions (up to about a pH of 7) and preferably under acidic conditions or with a pH of from about 1 to about 4. A micro-particulate filler material is then dispersed into the solution by means of stirring, sonification or other proper means or their combinations. Thereafter, an aqueous or organic silica sol is gradually added into the above solution while stirring to form a gel. The gel is then dried, preferably in shallow pans or in thin films, with a conventional gravity drying oven for a slow drying or furnace for quick drying. The dried powders are then collected and pulverized. The powder is next fired at a temperature and time sufficient to fuse the nano-particulate, pearl-like silica onto the micro-particulate glass or ceramic surfaces. The dried powder may be heated at about or above about 600° C. and preferably, the powder is heated at about or above about 800° C. to fuse the nano-particulate pearl-like silica onto the micro-particulate glass or ceramic surfaces. The fired particles are further subject to pulverization or milling to break the agglomerates and to surface silane treatment.

In these sol-derived hybrid fillers, the portion of material derived from the sol is present in an amount of less than or equal to about 90 percent by weight based on the total weight of the filler, with less than or equal to about 80 percent by weight preferred, and less than or equal to about 70 percent by weight more preferred. Also preferred is the portion of material derived from the sol present in an amount of greater than or equal to about 40 percent by weight, with greater than or equal to about 50 percent by weight more preferred, and greater than or equal to about 60 percent by weight based on the total weight of the filler especially preferred. The portion of the material derived from the opacifying metal oxide or calcinable precursor is present in an amount of less than or equal to about 20 percent by weight, with less than or equal to about 10 percent by weight preferred, and less than or equal to about 5 percent by weight more preferred. Also preferred is the portion of the material derived from the opacifying metal oxide or calcinable precursor compound present in an amount of greater than or equal to 0 percent by weight, with greater than or equal to about 1 percent by weight more preferred, and greater than or equal to about 2 percent by weight especially preferred.

In addition to the POSS filler and the sol-derived filler, the filler composition may further comprise one or more of the inorganic fillers currently used in dental restorative materials. Preferred additional fillers include those that are capable of being covalently bonded to the resin matrix itself or to a coupling agent that is covalently bonded to both. Examples of suitable filling materials include but are not limited to, silica, quartz, strontium silicate, strontium borosilicate, lithium silicate, lithium alumina silicate, amorphous silica, ammoniated or deammoniated calcium phosphate, tricalcium phosphate alumina, zirconia, tin oxide, and Titania. Some of the aforementioned inorganic filling materials and methods of preparation thereof are disclosed in U.S. Pat. No. 4,544,359 and U.S. Pat. No. 4,547,531, pertinent portions of which are incorporated herein by reference. Suitable high refractive index filler materials such as high refractive index silica glass fillers and calcium silicate based fillers such as apatites, hydroxyapatites or modified hydroxyapatite compositions may also be used. Alternatively, inert, non-toxic radiopaque materials such as bismuth oxide ($Bi_2O_3$), barium sulfate, and bismuth subcarbonate may be used. Suitable fillers have a particle size in the range from about 0.1 to about 5.0 microns, and may further comprise unbound, untreated silicate colloids of about 0.001 to about 0.07 microns. These additional fillers may also be silanized. Commercially available silane-treated fumed silica based on Aerosil A200 can be obtained from Degussa Corp under the names of Aerosil R711 and R7200.

The amount of total filler composition in the dental composite can vary widely, being in the range of about 1 to about 90 wt % of the total composition. The amount used is determined by the requirements of the particular application. Thus, for example, crown and bridge materials generally comprise from about 60 to about 90 wt % filler; luting cements comprise from about 20 to about 80 wt % filler; sealants generally comprise from about 1 to about 20 wt % filler; adhesives generally comprise from about 1 to about 30 wt % filler; and restorative materials comprise from about 50 to about 90 wt % filler, with the remainder in all cases being the resin composition and curing system.

The amount of POSS, sol-derived filler, and other filler in the filler composition relative to other filler may also vary widely, depending on the requirements of the particular application. Filler compositions may accordingly comprise about 0.1 to about 99 wt % POSS filler, about 0.5 to about 99.9 wt % sol-derived filler, and 0 to about 99.4 wt % other filler. More specifically, the filler compositions may comprise about 0.5 to about 30 wt % POSS filler, about 1 to about 60 wt % sol-derived filler, and about 10 to about 98.5 wt. % other filler. Even more specifically, the filler compositions may comprise about 1.0 to about 20 wt % POSS filler, about 5 to about 50 wt % sol-derived filler, and about 20 to about 60 wt. % other filler.

In one embodiment the type and amount of filler is adjusted so as to provide a flowable composition, that is, a composition that can readily be applied using a syringe or cannula. Such flowable compositions are of particular utility as sealing materials, tooth filling/restorative materials, cementing materials adhesives, and the like.

The low shrinkage, polymerizable dental resin may be used together with a curing system, which generally includes polymerization initiators; polymerization accelerators; ultraviolet light absorbers; antioxidants; and other additives known in the art.

Suitable polymerization initiators are those initiators, which can be utilized in UV-activated cure or visible light-activated cure compositions. For example, visible light curable compositions employ light-sensitive compounds, including but not being limited to benzil, benzoin, benzoin methyl ether, DL-camphorquinone (CQ), and benzil diketones. Either UV-activated cure or visible light-activated cure (approximately 230 to 750 nm) is acceptable. The amount of photoinitiator is selected according to the curing rate desired. A minimal catalytically effective amount is generally about 0.01 wt % of the total resin compositions, and will lead to a slower cure. Faster rates of cure are achieved with amounts of catalyst in the range from greater than about 0.01 percent to about 5 wt % of the dental composite material. The total resin composition is hereby defined as the total weight of the polymerizable dental resin and other resinous materials, such as for example, resinous diluents, which are used in the dental restorative material.

Alternatively, the dental restorative material may be formulated as self-curing and/or light curing systems. Self-curing dental composite materials will generally contain free radical polymerization initiators such as, for example, a peroxide in an amount of about 0.01 to about 1.0 wt % of the total resin dental composite material. Particularly suitable free radical initiators are lauryl peroxide, tributyl hydroperoxide and, more particularly benzoyl peroxide.

Polymerization accelerators suitable for use are the various organic tertiary amines well known in the art. In visible light curable dental composite materials, the tertiary amines are generally acrylate derivatives such as dimethylaminoethyl methacrylate and, particularly, diethylaminoethyl methacrylate (DEAEMA) in an amount of about 0.05 to about 0.5 wt % of the total dental composite material. In the self-curing dental composite materials, the tertiary amines are generally aromatic tertiary amines, preferably tertiary aromatic amines such as ethyl 4-(dimethylamino)benzoate (EDMAB), 2-[4-(dimethylamino)phenyl]ethanol, N,N-dimethyl-p-toluidine (DMPT), and bis(hydroxyethyl)-p-toluidine. Such accelerators are generally present in an amount of about 0.5 to about 4.0 wt % of the total dental composite material.

It is furthermore preferred to employ an ultraviolet absorber in an amount of about 0.05 to about 5.0 wt % of the total dental restorative material. Such UV absorbers are particularly desirable in the visible light curable dental restorative materials in order to avoid discoloration of the resin from incident ultraviolet light. Suitable UV absorbers are the various benzophenones, particularly UV-541, Tinuvin P, and Tinuvin 292, available from American Cyanamid Company and Ciba Specialty Chemicals Corp., respectively.

In a preferred embodiment, in one manner of proceeding, the polymerizable dental resin is prepared by reacting the multifunctional epoxide with the hydroxy acrylate and/or hydroxy methacrylate in the presence of a catalyst. The resulting polymerizable dental resin is then formulated into a dental restorative material by mixing with the filler composition and the curing system and applying to the tooth to be repaired.

Alternatively, the dental restorative material may be formulated as a two-part system, wherein the first part can comprise the low shrinkage, polymerizable dental resin, and the filler composition. The second part can comprise the curing system and optional diluent monomers. When necessary, the two parts are metered out and then mixed using a spatula. The cure may be initiated through the use of UV light or by raising the temperature of the mixture or chemical cure (self-cure). The dental restorative material thus obtained is then placed in the tooth to be repaired after it is appropriately prepared. Methods for use of the above-described compositions are well known in the art.

In one embodiment, in one manner of proceeding, the polymerizable resin composition (including any desired diluent monomers), the filler composition, and any additional additives are mixed. The curing system is added to the mixture, which is again stirred and stored or used, as appropriate. The cure may be initiated through the use of UV light or by raising the temperature of the mixture. The dental restorative resin thus obtained is then placed in the tooth to be restored after it is appropriately prepared. In one embodiment, the composition is flowable, and thus placed using a compule, cannula, or similar means. Methods for use of the above-described compositions are well known in the art.

In another embodiment, the dental composition is a glaze, in particular a glaze for use with temporary dental restorations. The glaze comprises a resin component and a filler component comprising a POSS filler. The resin component comprises a polymerizable, ethylenically unsaturated compound or mixture thereof. For example, the resin component may comprise a polymerizable oligomer comprising units of structure (I) and/or a viscous resin component such as Bis-GMA, DUDMA, PUDMA, EBPDMA, and the like. Preferably, the resin component is formulated to be of a relatively low viscosity, in order to allow application to the restoration by coating, for example with a brush. Relatively low viscosity oligomeric resins can therefore be used, for example aromatic or aliphatic polyurethane (meth)acrylates having a viscosity of about 100 to about 1000 centipoise (cps) at 60° C. The resins can be used with low viscosity diluent monomers as described above. Suitable diluent monomers include monofunctional or multifunctional (meth)acrylates having a viscosity of about 0.1 to about 200 cps at 25° C. Use of multifunctional (meth)acrylates can increase cure speed of the resin composition.

The relative amount of relatively low viscosity resin and diluent monomers is adjusted to provide the desired flowability and final properties, and will depend on the particular resins used, as well the type and amount of filler(s) used. Exemplary ratios of relatively low viscosity resin:diluent monomer are 99:1 to 1:99 by weight, more specifically 95:5 to 50:50, still more specifically 85:15 to 70:30 by weight.

The filler component is formulated to provide enhanced stain resistance to the glaze and comprises a POSS filler. In a preferred embodiment, the glaze consists essentially of a POSS filler. It has unexpectedly been found by the inventors hereof that POSS can be added to a glaze without significantly adversely affecting the clearness of the glaze, while at the same time improving the stain resistance of the glaze. Other fillers may accordingly be present in the filler composition, but only of a type and in an amount whereby a clear glaze is still produced, and stain resistance is not compromised. In one embodiment, the filler composition consists of a POSS filler.

The POSS used in the glaze is preferably reactive with at least one component of the resin composition. Preferred POSS fillers are of the formula $R_{n-m}T_nF_m$, wherein R is a hydrocarbon; n is 6, 8, 10, 12 or higher; m is 1 to n; T is $SiO_{1.5}$, and F is an organic group comprising a functional group reactive with at least one resin component. Preferred functional groups F are acrylate ($-X-OC(O)CH=CH_2$) and methacrylate ($-X-OC(O)CH(CH_3)=CH_2$) groups, wherein X is a divalent linking group having 1 to about 36 carbons, such as methylene, ethylene, propylene, isopropylene, butylene, isobutylene, phenylene, and the like. X may also be substituted with functional groups such as ether (e.g., $-CH_2CH_2OCH_2CH_2-$), as long as such functional groups do not interfere with formation or use of the POSS. X is preferably propylene, isobutylene, or $-OSi(CH_3)_2CH_2CH_2CH_2-$.

The relative amounts of the resin composition and the filler composition are adjusted to provide the desired flowability and final properties, and will depend on the particular resins used, as well at the type and amount of filler(s) used. Exemplary ratios of resin composition:filler composition are 99.5:0.5 to 80:20 by weight, more specifically 99:1 to 90:10, still more specifically 98:2 to 93:7.

The glaze further comprises a curing system. Where the resin is (meth)acrylate-functionalized, the curing system comprises a polymerization initiator and optional polymerization accelerators as described above. The glaze can further optionally further comprises a stabilizer, UV absorber, colorant, medicaments, a fluoride source, and/or other additives known in the art.

The invention is further illustrated by the following non-limiting examples. Unless otherwise specified, the amount of each component of the formulations shown in the Tables are in parts by weight.

EXAMPLE 1

Samples of a bisphenol A monomer comprising an epoxy and a methacrylate group (bisphenol A epoxy/methacrylate, "BAEM") (Samples 1-3) or bisphenol F epoxy/methacrylate (BFEM) (Samples 4-6) were prepared by reacting either the diglycidyl ether of bisphenol A (DGEBA) or the diglycidyl ether of bisphenol F (DGEBF) with 2-hydroxyethyl methacrylate (HEMA), all obtained from Sigma-Aldrich, in the molar ratios of HEMA with epoxy shown in Table 1.

The mixture was stirred using a magnetic stirrer. The flask was maintained in an oil bath at a temperature of 130-170° C. during the course of the reaction. The reaction was catalyzed by the addition of 5 mole % (based on the total moles of the reactants) of stannous 2-ethylhexanoate (SEH) also obtained from Sigma-Aldrich. The total time of the reaction was from 2 to 8 hours. The reaction was monitored by FTIR and stopped when the intensity of C—O stretching in oxirane ring at 910 $cm^{-1}$ did not decrease significantly.

TABLE 1

| Sample No. | mole % of HEMA to epoxy | BAEM or BFEM |
|---|---|---|
| 1 | 0.25 | BAEM1 |
| 2 | 0.50 | BAEM2 |
| 3 | 0.75 | BAEM3 |
| 4 | 0.25 | BFEM1 |
| 5 | 0.50 | BFEM2 |
| 6 | 0.75 | BFEM3 |

EXAMPLE 2

All the resin or resin combinations shown in Table 2 below were mixed with 3 wt % diaryliodonium hexafluoro antimonite commercially available from Sartomer Company, 0.3 wt % camphorquinone (CQ) obtained from Aldrich Chemicals Company and 0.2 wt % ethyl 4-(dimethylamino)benzoate (EDMAB) commercially available from Aldrich. Sample 11 is a comparative example and represents a blend of 70 wt % epoxy resin (DGEBA) with 30 wt % of an acrylate resin i.e., ethoxylated bisphenol A dimethacrylate (EBPADMA), while samples 12 and 13 represent a blend of the polymerizable dental resin of this disclosure i.e., 70 wt % BAEM1 or BAEM2 resin with 30 wt % EBPADMA, wherein the wt % is calculated with respect to the total weights of the respective BAEM resin and EBPADMA.

A small amount of the resin of each sample (0.2 grams) was placed in a mixing well and was cured using a visible light source Cure-Lite™ (commercially available from Pentron Corp.) for different time periods. Gel time is the time taken by the resin to reach an infinite viscosity and was determined using a spatula in the mixing well. Hardening time is the time taken by the resin to attain a hardened mass felt by touching with a spatula.

TABLE 2

| Sample No. | Composition | Gel Time | Hardening Time |
|---|---|---|---|
| 7 | DGEBA | 1 minute | 2 minutes |
| 8 | DGEBF | 6 minutes | 12 minutes |
| 9 | BAEM1 | 1 second | 5 minutes |
| 10 | BAEM2 | 1 second | 2 minutes |
| 11 | DGEBA/EBPADMA (70/30 wt. ratio) | 1 second | 4 minutes |
| 12 | BAEM1/EBPADMA (70/30 wt. ratio) | 1 second | 30 seconds |
| 13 | BAEM2/EBPADMA (70/30 wt. ratio) | 1 second | 12 seconds |
| 14 | EBPADMA | 1 second | 12 seconds |

As can be seen in Table 2, samples 9 and 10 obtained by the reaction of DGEBA with HEMA reach the gel point much more rapidly than the samples 7 and 8 obtained by reacting the epoxy precursors DGEBA and DGEBF respectively. Sample 11, which represents a blend of an epoxy resin with an acrylate resin gels within 1 second as do samples 12 and 13, which are blends of the polymerizable dental resin of this disclosure with EBPADMA. However, both samples 12 and 13 takes a much shorter time (approximately 30 seconds or less) to reach a hardened mass as compared with sample 11, which takes approximately 4 minutes. Thus blends comprising the polymerizable dental resin can generally be cured in a much shorter time period than the corresponding comparative blend.

EXAMPLE 3

Samples 15-17 were made by mixing BAEM1 with EBPADMA in different weight ratios as indicated in Table 3. These samples were cured by utilizing a curing system comprising 3% wt % diaryliodonium hexafluoro antimonite (SarCat®CD 1012, Sartomer Corp.), 0.3 wt % camphorquinone (CQ) and 0.2 wt % EDMAB where the percentages are calculated with respect to the total weight of the composition. Three point bending strength or flexural strength was measured on all samples using an ATS machine as per ISO 4049 for Resin Based Filling Materials (1997). The samples were cured for a total four minutes using visible light with CureLite™ Plus curing box (Pentron Corp.) Samples were then trimmed and stored in water at 37° C. for 24 hours before testing. The results are listed in Table 3.

TABLE 3

| Sample No. | Resin or resin combinations | Flexural strength in psi (standard deviation) |
|---|---|---|
| 15 | BAEM1/EBPADMA (70/30 wt ratio) | 18985 (941) |
| 16 | BAEM1/EBPADMA (50/50 wt ratio) | 18182 (1383) |
| 17 | BAEM1/EBPADMA (30/70 wt ratio) | 18631 (1128) |
| 18 | EBPADMA | 4571 (739) |

Table 3 clearly shows that the blends containing the BAEM and EBPADMA have superior flexural strength than those samples obtained by curing the EBPADMA alone.

The low shrinkage, polymerizable dental resin or blends comprising the polymerizable dental resin thus display a number of advantages over other resins used in dental composite materials. These resins or the blends comprising these resins generally display a shrinkage of less than or equal to about 8, preferably less than or equal to about 6, more preferably less than or equal to about 4, and most preferably less than or equal to about 2 volume percent upon curing as compared with the volume occupied prior to curing. The polymerizable dental resins or blends comprising these resins also display a flexural strength greater than or equal to about 15,000, preferably greater than or equal to about 16,000, more preferably greater than or equal to about 17,000, and most preferably greater than or equal to about 18,000 psi (pounds per square inch) upon curing with the Cure-Lite™ curing unit for a time period of about 2 to about 5 minutes.

EXAMPLE 4

A dental composite containing an epoxy/methacrylate resins BAEM1 from Example 1 and an ethoxylated$_6$ bisphenol A dimethacrylate available under the trade designation CD541 from Sartomer in 50/50 wt % ratio was prepared. The resin contains cationic and free radical initiators of 3 wt % diaryliodonium hexafluoro antimonite (SarCat®CD 1012), 0.4% CQ and 0.8% EDMAB. The paste is composed of 26% resin, 2% silane treated OX50 (Degussa Corp.), 52% silane treated barium glass filler with an average particle size of 0.7 micrometers (Schott Glass) and 20% zirconium silicate filler. Shrinkage was measured using a mercury dilatometer developed by NIST. The shrinkage of this composite is about 1.5% by volume upon setting. As a comparison, a composite product available under the trade designation SIMILE™ (Pentron Corp.) with a similar filler composition was also tested. The shrinkage of the SIMILE™ composite is about 2.3 % by volume.

EXAMPLE 5

A bromine-containing methacrylate/epoxy resin was synthesized from the reaction of HEMA or CLMA with brominated bisphenol A diglycidyl ether (BRDGEBA) using the same method as described in Example 1. The molar ratio of hydroxyl group to epoxy was 0.5. The resulting methacrylate/epoxy resin from HEMA and CLMA are abbreviated as BRBAEM1 and BRBAEM2, respectively.

EXAMPLE 6

Resin combinations of BRBAEM2 and EBPADMA in 50/50 wt % ratio with different initiation systems were prepared and their flexural strengths were compared as shown in Table 4. In Sample 19, both cationic polymerization of epoxy and free radical polymerization of methacrylate were utilized. In Sample 20, only free radical polymerization of methacrylate was utilized.

TABLE 4

| Sample No. | Initiating System | Flexural Strength (psi) |
|---|---|---|
| 19 | 3% CD1012, 0.3% CQ, 0.2% EDMAB | 15934 (791) |
| 20 | 0.3% CQ, 0.2% EDMAB | 15105 (972) |

Table 4 shows no difference between the strength of Sample 19 and Sample 20. The addition of cationic photo initiator does not increase the strength in this case.

EXAMPLE 7

Dental composite (Sample 21) containing an epoxy/methacrylate resin BREPMA2 and an ethoxylated$_6$ bisphenol A dimethacrylate available under the tradename CD541 (Sartomer) in 50/50 wt % ratio was prepared. Shrinkage as well as strength was tested. As a comparison, a paste (Sample 22) containing a commercial resin system (SIMILE™, (Pentron Corp.) having a combination of BisGMA/PCBisGMA/UDMA/HDDMA (each of 25%) was also prepared and tested. In both resin systems, no cationic photoinitiator was added. Both resins contain free radical initiators 0.3% CQ and 0.6% EDMAB. Both Samples 21 and 22 have 35 wt % resin, 10 wt % Aerosil R 7200 (Degussa) and 55 wt % zirconium silicate filler as above. The modulus of rupture (MOR), an indicator of flexural strength, and shrinkage of these two composites are compared in Table 5. Shrinkage was measured using a mercury dilatometer developed by NIST. Results are shown below in Table 5.

TABLE 5

| Sample No. | MOR (psi) | Shrinkage |
|---|---|---|
| 21 | 16023 (1624) | 1.9 |
| 22 | 16197 (1533) | 2.8 |

EXAMPLE 8

A resin was prepared by combining, in parts by weight, 10.5 parts BAHEMA, 19.25 parts EBPADMA, 0.007 parts 2,6-di-t-butyl-4-methyl phenol antioxidant (BHT), 0.35 parts UV-5411 stabilizer, 0.0035 parts UV-OB stabilizer, 0.175 parts Lucirin™ TPO (2,4,6-trimethylbenzoyldiphenylphosphine oxide photoinitiator from BASF), 0.035 parts camphorquinone, 0.105 parts EDMAB, 3 parts POSS filler of the formula $(Ph)_7(SiO_{1.5})_4D_4(OH)_3$ (POSS SO 1458), 0.3 parts BiOCl, 20.4 parts silane-treated zirconium silicate nanofiller, 40.8 parts silane-treated Bad-B—Al—F-silicate glass filler, 0.5 parts silane-treated amorphous silica and less than 0.1 part pigments (FDC #5, red iron oxide and black iron oxide).

A resin matrix was prepared wherein the BAHEMA, EBPADMA, and HDDMA were mixed together with stirring. Photoinitiators (camphorquinone, EDMAB and Lucirin™ TPO) and other additives (UV absorber, antioxidant, etc.) were added into the resin mix and allowed to dissolve completely. The POSS, BiOCl, the silane-treated fillers, and pigments were then added and thoroughly incorporated. A visible light cured dental material based on this composition was tested according to ISO 4049 for the mechanical and physical properties of flexural strength (MOR), compressive strength (CS), water sorption and water solubility (wt. loss). Vicker's Microhardness (VH) was measured using Clark™ Hardness Tester (Clark Instrument Inc.). A commercial dental flowable composite product is used as a reference. The property comparison is in Table 6.

TABLE 6

| Property | Comparative Composite | Nanohybrid Composite |
|---|---|---|
| MOR (MPa) | 125 (11) | 120 (10) |
| CS (MPa) | 309 (12) | 332 (26) |
| VH (Kg/mm$^2$) | 26 (1) | 35 (3) |
| Water Sorption/Wt. Loss (µg/mm$^3$/week) | 12/3 | 10/2 |

Polymerization of the nanohybrid composition upon visible light curing was further evaluated and compared to various commercial visible light curable flowable composite products (Flow-it! ALC (Pentron); Four Seasons Flow (Ivoclar-Vivadent, Liechtenstein); and Esthet.x Flow (Dentsply, Milford, Del.)). The shrinkage (vol %) for each sample upon curing was measured by a mercury dilatometer developed by the National Institute of Standards and Technology (NIST). Due to difficulties in evaluating the shrinkages of flowable, low viscosity compositions with the dilatometer, each of the flowable materials were further thickened by the addition of 14% by volume of untreated OX50 silica (Degussa Corp.) to form putty-like pastes. The final shrinkage values of the flowable materials were then calculated with the measured shrinkage multiply by 1.16. The shrinkage results for the various flowable materials are shown in Table 7.

TABLE 7

| | Nanohybrid composition | Flow-It! ALC A2 Shade (Lot# 114528) | 4 Seasons Flow A2, Enamel (Lot G022073) | Esthet.x Flow A2 Shade (Lot# 040331) |
|---|---|---|---|---|
| Shrinkage by Volume (%) | 3.1 | 4.0 | 3.8 | 4.0 |

EXAMPLE 9

Stain Resistance

Table 8 below shows the formulations of illustrative glaze compositions comprising POSS fillers as described herein (Samples B-D), as well as a comparative composition without POSS filler (Sample A). When applied in a thin layer, the resin compositions of Table 8 are all visible light curable in about 30 seconds using either a dental light emitting diode (LED) or halogen light. The surfaces of the cured resin compositions are tack-free and glossy.

TABLE 8

| Components | A* | B | C | D |
|---|---|---|---|---|
| Hexafunctional aromatic urethane acrylate (MW approx. 800, CN 975, Sartomer) | 78.6 | 78.6 | 78.6 | 78.6 |
| Trifunctional acrylate resin (SR 9012, Sartomer) | 8.3 | 8.3 | 8.3 | 8.3 |
| Tetrahydrofurfurylmethacrylate | 8.5 | 8.5 | 8.5 | 8.5 |
| Gamma-methacryloxypropyl trimethoxysilane | 1.2 | 1.2 | 1.2 | 1.2 |
| UV absorber (UV-5411) | 0.75 | 0.75 | 0.75 | 0.75 |
| UV absorber (UV-OB) | 0.01 | 0.01 | 0.01 | 0.01 |
| CQ | 0.17 | 0.17 | 0.17 | 0.17 |
| EDMAB | 0.47 | 0.47 | 0.47 | 0.47 |
| Photoinitiator (Lucirin ™ TPO, BASF) | 2.0 | 2.0 | 2.0 | 2.0 |
| POSS(SO 1458, technical grade, from Hybrid Plastics) | 0 | 2 | 0 | 5 |
| POSS (MA 0735 from Hybrid Plastics) | 0 | 0 | 2 | 0 |

*Comparative composition

Each of the resin compositions of Table 8 were formed into discs by placing the resin into the interior of a mold having a diameter of 15 millimeters (mm) and thickness of about 1 mm, and that was situated between two glass slides. The resin compositions were cured by exposure to UV light. The cured discs were removed from the mold and used to test for staining resistance. Two disks were prepared for each material for each stain resistance test. In addition to compositions A-D of Table 8, an additional control composition (Sample E) was formed into discs. Sample E was a commercially available, (meth)acrylate crown and bridge light curable glaze containing no filler.

Stain resistance tests were performed by submerging each sample disc halfway into two different solutions for durations of one hour and three 3 days, respectively, in an incubator set at 37° C. The first solution was a coffee solution made using one pre-measured/packed single bag per cup, and the second solution was a 2 weight % curry powder in water. A Seradyn ColorWalk™ calorimeter (Photovolt Instrument) was used to measure the colors of the discs. Before each measurement, the samples were rinsed with tap water and dried. Color measurements were made before submerging the samples into the solutions, after one hour of submersion and after three days of submersion. The color scales of L*, a*, b* were recorded and ΔE was calculated based on the color change between the samples before and after testing. The average ΔE numbers for each test group are presented in Table 9 below. A higher ΔE value (increased color change) means lower stain resistance.

TABLE 9

| Sample | Coffee (one hr), ΔE | Coffee (3 days), ΔE | Curry (one hr), ΔE | Curry (3 days), ΔE |
|---|---|---|---|---|
| A* | 2.5 | 3.4 | 11.1 | 42.3 |
| B | 1.2 | 2.4 | 4.9 | 38.2 |
| C | 1.8 | 2.6 | 3.3 | 37.7 |
| D | 1.5 | 2.5 | 3.6 | 31.7 |
| E* | 2.2 | 4.4 | 13.2 | 45.5 |

*Controls

The data of Table 9 shows that the compositions comprising POSS filler surprisingly resisted staining upon both short-term and long-term exposure to coffee and curry better than compositions without the filler.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A polymerizable dental glaze, comprising:
   a polymerizable, ethylenically unsaturated resin composition;
   a filler composition consisting essentially of a polyhedral oligomeric silsesquioxane filler; and
   a curing system.

2. The dental glaze of claim 1, wherein the resin composition comprises a relatively low viscosity resin and a diluent monomer composition.

3. The dental glaze of claim 1, wherein the weight ratio of the relatively low viscosity resin:diluent monomer composition is about 99:1 to about 50:50.

4. The dental glaze of claim 1, wherein the relatively low viscosity resin is an aromatic urethane (meth)acrylate, and the diluent monomer comprises a multifunctional (meth)acrylate.

5. The dental glaze of claim 1, wherein the polyhedral oligomeric silsesquioxane filler has the formula $(RSiO_{3/2})_n$, wherein R is a hydrocarbon and n is 6, 8, 10, 12, or 14.

6. The dental glaze of claim 1, wherein the polyhedral oligomeric silsesquioxane filler has the formula $R_{n-m}T_nF_m$, wherein R is a $C_1$-$C_{24}$ straight, branched, or cyclic alkyl group, or a $C_6$-$C_{24}$ aromatic, alkylaryl, or arylalkyl group, wherein the alkyl or aromatic groups are optionally substituted with $C_1$-$C_6$ alkyl, halo, $C_1$-$C_6$ alkoxy, or $C_1$-$C_6$ perhaloalkyl; n is 6, 8, 10, 12, or 14; m is 1 to n; T is $SiO_{3/2}$; and F is an organic group comprising a functional group reactive with a component of the resin composition.

7. The dental glaze of claim 6, wherein the functional group is a (meth)acrylate.

8. The dental glaze of claim 7, wherein F has the formula —X—OC(O)CH=$CH_2$ or —X—OC(O)CH($CH_3$)=$CH_2$, wherein X is a divalent linking group having 1 to about 36 carbon atoms.

9. The dental glaze of claim 8, wherein X is methylene, ethylene, propylene, isopropylene, butylene, isobutylene, phenylene, or —$CH_2CH_2OCH_2CH_2$—, or —$OSi(CH_3)_2CH_2CH_2CH_2$—.

10. The dental glaze of claim 1, wherein the polyhedral oligomeric silsesquioxane filler has the formula $R_{n+p}T_{n-p-1}D_p(OL)_p$, wherein is a $C_1$-$C_{24}$ straight, branched, or cyclic alkyl group, or a $C_6$-$C_{24}$ aromatic, alkylaryl, or arylalkyl group, wherein the alkyl or aromatic groups are optionally substituted with $C_1$-$C_6$ alkyl, halo, $C_1$-$C_6$ alkoxy, or $C_1$-$C_6$ perhaloalkyl; T is $SiO_{3/2}$; D is $SiO_{2/2}$; L is hydrogen or a hydrocarbon comprising a functional group reactive with a component of the resin composition; and p is a multiple of 3.

11. The dental glaze of claim 10, wherein the functional group is a (meth)acrylate.

12. The dental glaze of claim 10, wherein L is hydrogen.

13. The dental glaze of claim 12, wherein R is an unsubstituted $C_6$-$C_{24}$ aromatic, alkylaryl, or arylalkyl group.

14. The dental glaze of claim 1, wherein the ratio of resin composition:filler composition is 99.5:0.5 to 80:20 by weight.

15. The dental glaze of claim 1, wherein the ratio of resin composition:filler composition is 99:1 to 90:10 by weight.

16. A method of manufacturing a polymerizable dental glaze, comprising combining:
   a polymerizable, ethylenically unsaturated resin composition;
   a filler composition consisting essentially of a polyhedral oligomeric silsesquioxane filler; and
   a curing system.

17. A method of making a dental restoration, comprising
   applying to dental restoration a polymerizable dental glaze comprising
      a polymerizable, ethylenically unsaturated resin composition;
      a filler composition consisting essentially of a polyhedral oligomeric silsesquioxane filler; and
      a curing system; and
   curing the glaze.

18. The method of claim 17, wherein the dental restoration is a temporary dental restoration.

19. The method of claim 17, wherein the dental restoration is a permanent dental restoration.

* * * * *